(12) United States Patent
Wang et al.

(10) Patent No.: US 10,818,010 B2
(45) Date of Patent: Oct. 27, 2020

(54) DEVICE, SYSTEM AND METHOD FOR SKIN DETECTION

(71) Applicant: KONINKLIJKE PHILIPS N.V., Eindhoven (NL)

(72) Inventors: Wenjin Wang, Utrecht (NL); Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/074,437

(22) PCT Filed: Feb. 8, 2017

(86) PCT No.: PCT/EP2017/052748
§ 371 (c)(1),
(2) Date: Aug. 1, 2018

(87) PCT Pub. No.: WO2017/137435
PCT Pub. Date: Aug. 17, 2017

(65) Prior Publication Data
US 2019/0057502 A1 Feb. 21, 2019

(30) Foreign Application Priority Data
Feb. 8, 2016 (EP) .................................... 16154665

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0077* (2013.01); *A61B 5/0261* (2013.01);
(Continued)

(58) Field of Classification Search
CPC . G06T 7/0012; A61B 5/0077; A61B 5/02416; A61B 5/0261; A61B 5/0295; G06K 9/6284; G06K 9/6298
See application file for complete search history.

(56) References Cited

U.S. PATENT DOCUMENTS

| 2005/0171439 | A1* | 8/2005 | Maschke | .............. | A61B 5/0066 |
| | | | | | 600/476 |
| 2007/0106160 | A1* | 5/2007 | Kilgore | .............. | G06K 9/00255 |
| | | | | | 600/473 |

(Continued)

FOREIGN PATENT DOCUMENTS

| WO | 2014/095759 | 6/2014 |
| WO | 2015/049150 | 4/2015 |

OTHER PUBLICATIONS

Wang, et al., "Exploiting Spatial Redundancy of Image Sensor for Motion Robust rPPG", IEEE Transactions on Biomedical Engineering, vol. 62, No. 2, Feb. 2015.

(Continued)

*Primary Examiner* — Md K Talukder

(57) ABSTRACT

The present invention relates to a device, system and method for skin detection. To enable a reliable, accurate and fast detection the proposed device comprises an input interface (30) for obtaining image data of a scene, said image data comprising a time sequence of image frames, an extraction unit (31) for extracting a photoplethysmography (PPG) signal from a region of interest of said image data, a transformation unit (32) for transforming said PPG signal into a spectral signal, a sorting unit (33) for sorting said spectral signal to obtain a sorted spectral signal representing a descriptor, and a classifier (34) for classifying said region of interest as skin region of a living being or as non-skin region based on the descriptor.

10 Claims, 6 Drawing Sheets

(51) Int. Cl.
*A61B 5/00* (2006.01)
*A61B 5/024* (2006.01)
*A61B 5/026* (2006.01)
*A61B 5/0295* (2006.01)
*G06K 9/62* (2006.01)

(52) U.S. Cl.
CPC ........ *A61B 5/0295* (2013.01); *A61B 5/02416* (2013.01); *G06K 9/6284* (2013.01); *G06K 9/6298* (2013.01); *A61B 5/0075* (2013.01); *A61B 5/02433* (2013.01); *A61B 5/02438* (2013.01); *A61B 5/7203* (2013.01); *A61B 5/7267* (2013.01); *G06T 2207/20216* (2013.01); *G06T 2207/30076* (2013.01); *G06T 2207/30088* (2013.01)

(56) References Cited

U.S. PATENT DOCUMENTS

| | | | | |
|---|---|---|---|---|
| 2009/0005700 | A1* | 1/2009 | Joshi | A61B 5/0488 600/546 |
| 2013/0271591 | A1 | 10/2013 | Van Leest | |
| 2013/0296660 | A1 | 11/2013 | Tsien | |
| 2013/0342702 | A1* | 12/2013 | Zhang | G06K 9/00255 348/164 |
| 2015/0282724 | A1* | 10/2015 | McDuff | A61B 5/02427 600/479 |
| 2015/0302158 | A1 | 10/2015 | Morris | |
| 2016/0089041 | A1* | 3/2016 | Keat | A61B 5/72 600/479 |
| 2016/0120482 | A1* | 5/2016 | Kirenko | A61B 5/02416 600/479 |
| 2016/0220128 | A1* | 8/2016 | Den Brinker | A61B 5/7203 |
| 2019/0057502 | A1* | 2/2019 | Wang | A61B 5/0295 |

OTHER PUBLICATIONS

Verkruysse et al., "Remote plethysmographic imaging using ambient light", Optics Express, 16(26), Dec. 22, 2008, pp. 21434-21445.
G. de Haan and A. van Leest, "Improved motion robustness of remote-PPG by using the blood volume pulse signature", Physiol. Meas. 35 1913, 2014.
Wang, et al., "Unsupervised Subject Detection via Remote PPG", IEEE Transactions on Biomedical Engineering, vol. 62, Issue: 11, Nov. 2015.
Van Luijtelaar, et al., "Automatic ROI Detection for Camera-based Pulse-rate Measurement", The 12th Asian Conference on Computer Vision (ACCV' 14), Int. Workshop on Video Segmentation in Computer Vision, W10-p3, Nov. 1-5, 2014, Singapore.
http://www.dailymail.co.uk/news/article-1345756/Eight-arrested-Hong-Kong-connection-Canadian-people-smuggling-case.html; Jan. 2011.
Kumar, et al., "DistancePPG: Robust non-contact vital signs monitoring using a camera"; Biomedical Optics Express. 2015.
Docampo, "Heart rate estimation using facial video information"; 2012.

* cited by examiner

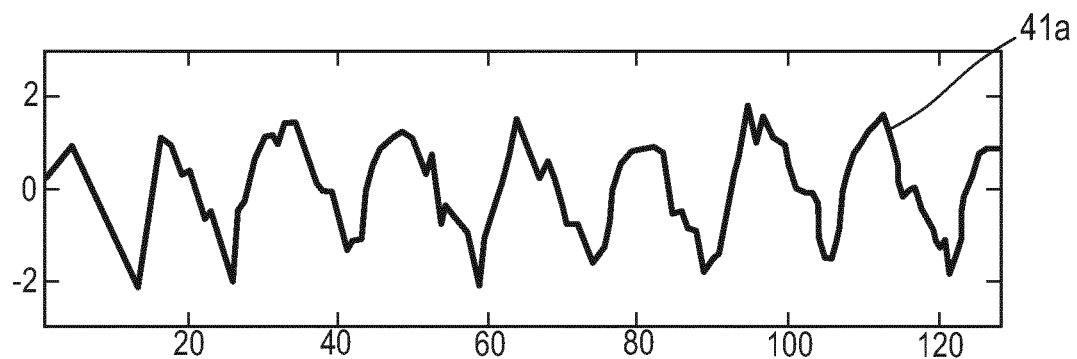
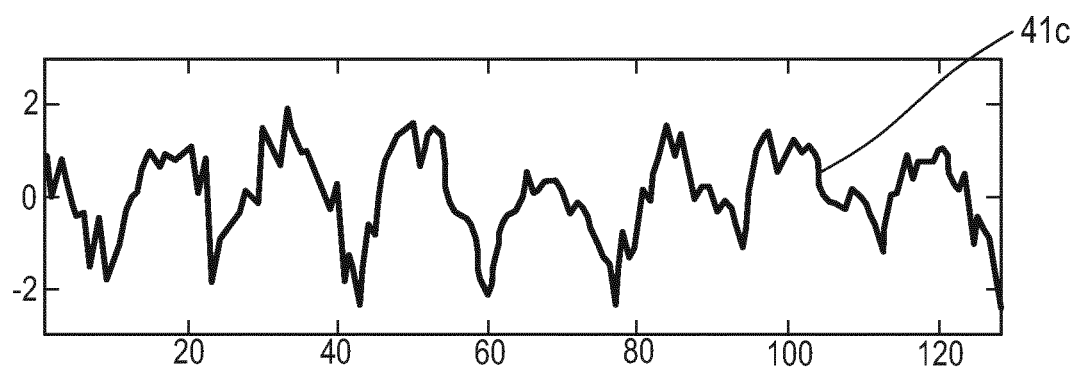
FIG.3A
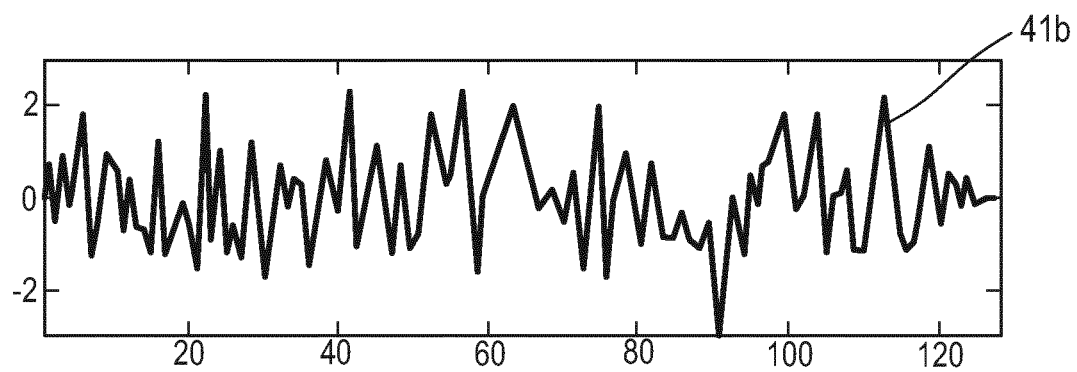
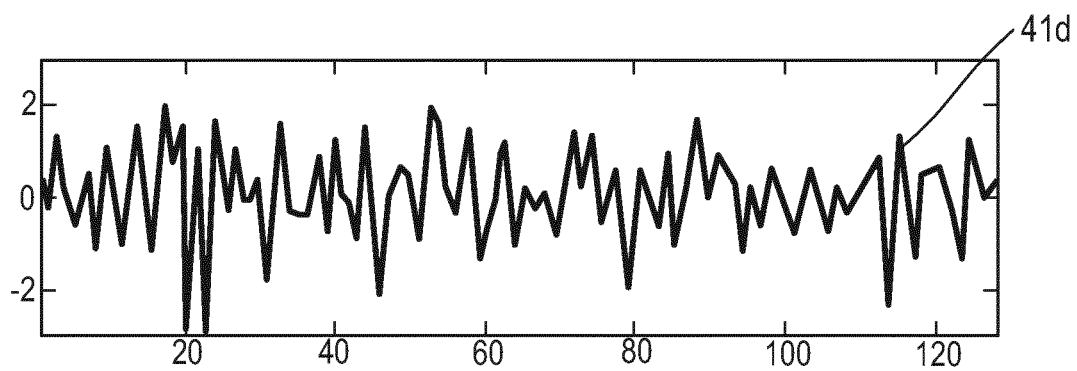
FIG.3B

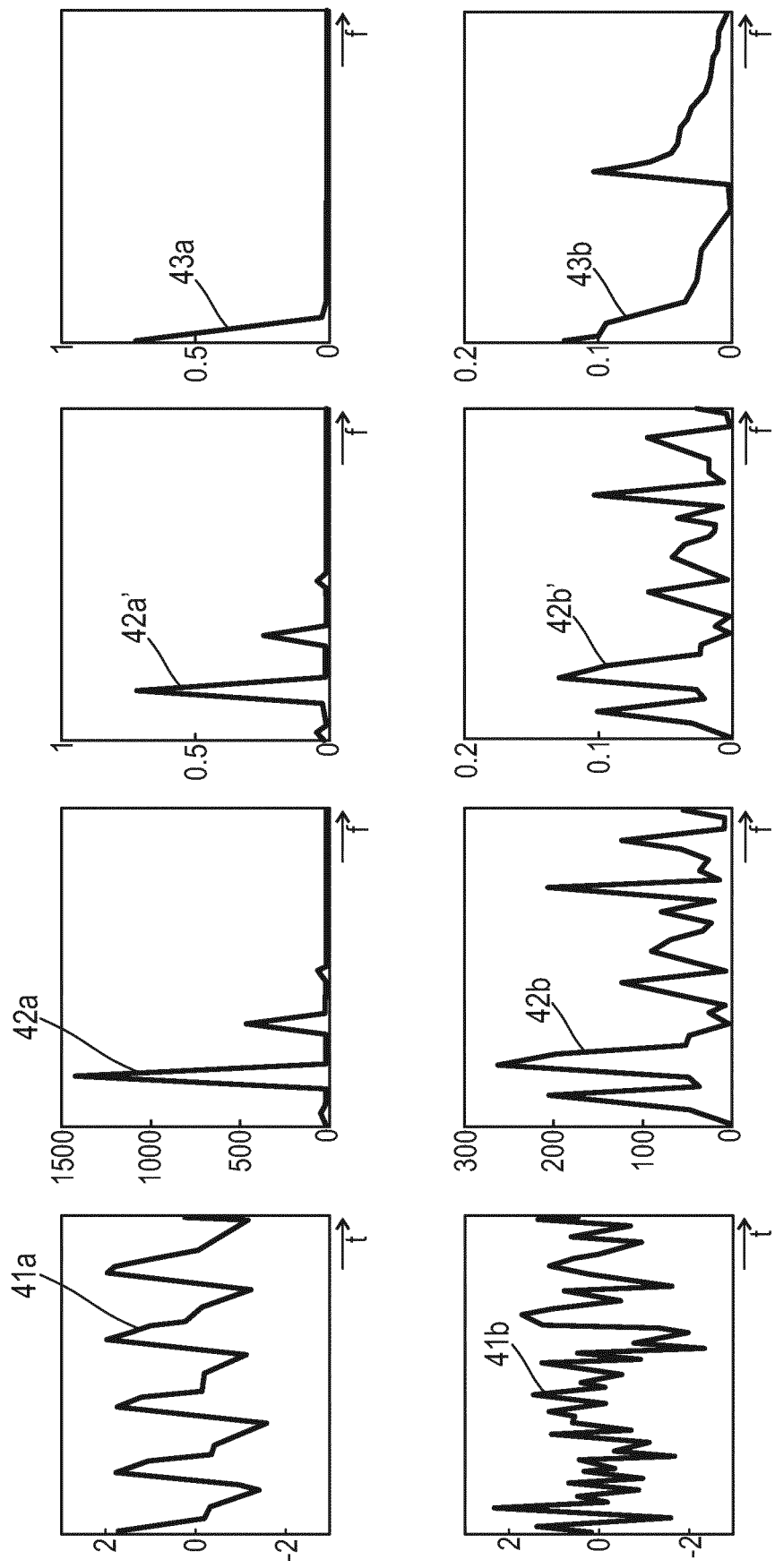

DEVICE, SYSTEM AND METHOD FOR SKIN DETECTION

CROSS REFERENCE TO RELATED APPLICATIONS

This application is the U.S. National Phase application under 35 U.S.C. § 371 of International Application No. PCT/EP2017/052748, filed Feb. 8, 2017, published as WO 2017/137435 on Aug. 17, 2017, which claims the benefit of European Patent Application Number 16154665.0 filed Feb. 8, 2016. These applications are hereby incorporated by reference herein.

FIELD OF THE INVENTION

The present invention relates to a device, system and method for skin detection.

BACKGROUND OF THE INVENTION

Vitas signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen (or other blood gasses/substances) saturation can be determined.

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin, premature babies, or patients with extensive burns.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Apart from the advantage of being fully contactless, cameras (generally called imaging devices) provide 2D information, which allows for a multi-spot and large area measurement, and often contains additional context information. Unlike contact sensors, which rely on the correct placement on a specific measurement point/area, the regions used to measure pulse signals using rPPG technology are determined from the actual image. Therefore, accurate detection of skin areas, reliable under any illumination conditions becomes a crucial part in the processing chain of a camera-based rPPG device and method.

Currently, there are two main approaches known for reliable detection and tracking of a skin areas.

One approach is based on skin color (RGB-based) detection and segmentation. Methods according to this approach are fast in both detection and tracking of areas with skin color. However, they are not robust to changes of ambient light color, which will change the color of light reflected from a skin area, and are not able to detect skin areas under low illumination conditions or in darkness. Moreover, such methods cannot always differentiate skin from other surfaces with the same color.

Another approach is based on extracted PPG signals (PPG-based). Methods according to this approach are more robust in differentiating real skin areas and areas of other object of the same skin color. This approach can be used also to segment the skin areas, which have stronger PPG signal (the most periodic signal). However, the reliability of the approach depends on the robustness of PPG signal extractions, thus it is impacted by motion of a subject and the blood perfusion level. Therefore, if a pulse signal is not periodic or weak, a camera-based system will have difficulties to detect/segment the skin areas. Moreover, the approach is computationally expensive.

It should be noted that the detection of skin area is not only of interest in the field of vital signs detection based on the rPPG technology, but also in other technical fields, e.g. in remote gaming applications using camera technology to recognize gestures of the player, face detection, security (robust detection of a person using surveillance cameras and detection of a person wearing a mask or distinguishing real faces from a realistic mask in a camera registration), etc.

It has been shown that the periodic color change itself in acquired images can be used to distinguish between skin and non-skin of a living being. However, particularly for applications with low light level or in the dark, e.g. for night-time patient monitoring, the relatively low amplitude of these absorption variations, particularly in the near-infrared (NIR) wavelength range, is still problematic and causes practical attempts to fail distinguishing skin and non-skin.

WO 2015/049150 A1 relates to a device for processing of input signals related to a vital sign of a subject, the device comprising an interface for receiving a non-invasively detected input signal, a feature extraction module for extracting at least one feature of the input signal, said at least one feature including an instantaneous frequency and/or amplitude representation of the input signal, a processing module for determining a signal information content parameter for the input signal based on the at least one extracted feature, said signal information content parameter being indicative of information on a vital sign of the subject included in the input signal and a combination module for combining a plurality of input signals based on the signal information content parameters of the plurality of input signals into a combined output signal characterizing the vital sign of the subject. D1 further relates to a corresponding method and to a monitoring system for remotely monitoring a vital sign of a subject.

US 2013/0296660 A1 describes methods and systems for remotely measuring or monitoring one or more physiological parameters in a subject, such as blood volume pulse, heart rate, respiratory wave, or respiration rate. The methods include capturing a series of images of the subject, and processing the images to obtain physiological parameters of interest. These methods can be used to analyze single channel signals, including signals obtained from active night vision cameras. As a result, these methods can be used to measure or monitor one or more physiological parameters in both daylight and low-light conditions.

SUMMARY OF THE INVENTION

It is an object of the present invention to provide a device and a corresponding method as well as a system which allow a reliable, accurate and fast detection of skin, in particular for use in a device and method for detecting vital signs of a subject.

In a first aspect of the present invention a device for skin detection is presented comprising an input interface for obtaining image data of a scene, said image data comprising a time sequence of image frames, an extraction unit for extracting a photoplethysmography, PPG, signal from a region of interest of said image data, a transformation unit for transforming said PPG signal into a spectral signal, a sorting unit for sorting said spectral signal to obtain a sorted spectral signal representing a descriptor, and a classifier for classifying said region of interest as skin region of a living being or as non-skin region based on the descriptor.

In a further aspect of the present invention a corresponding method is presented.

In a yet further aspect of the present invention a system for skin detection is presented comprising an imaging unit for acquiring image data of a scene and a device for skin detection as disclosed herein based on the acquired image data of the scene.

In yet further aspects of the present invention, there are provided a computer program comprising program code means for causing a computer to carry out the steps of the method as disclosed herein when said computer program is carried out by the computer, as well as a non-transitory computer-readable recording medium that stores therein a computer program product, which, when executed by a computer, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The present invention is based on the idea to distinguish a pulse signal from noise in the frequency domain, for instance by evaluating the distribution of the energy in a sorted frequency domain signal derived from image data of a scene potentially including a skin are of a living being or even a complete living being or different body parts showing skin areas and non-skin areas. It has particularly been found that the energy of a pulse signal (in a sorted (or ranked) frequency domain representation) drops faster than the energy of the sorted (or ranked) noise spectrum. With a classifier, that is preferably trained accordingly e.g. using such ranked spectra as input, a reliable decision can be made whether or not a particular region of interest (ROI) in the image data, e.g. an image segment of the image frames of said image data, shows skin or not.

Hereby, sorting and ranking shall be understood as synonyms. It means that the order of the frequency samples is changed so that they appear ordered with a decreasing or increasing amplitude, i.e. the frequency samples are re-ordered in frequency direction.

Hence, the proposed device, system and method enable determining whether a 3D time series of image frames (particularly image segments therein) contains alive human tissue or not by substantially extracting a 1D time signal (also called "PPG signal" herein) from the 3D time series of image frames, transforming the time signal into a transformed signal and sort the transformed signal to obtain a descriptor, and classifying the 3D time series of image frames based on the descriptor.

It shall be noted in this context that at the time of extracting the PPG signal from a ROI of said image data, e.g. from a ROI in a video sequence, it is not known if the ROI actually shows skin or not. Despite that uncertainty, the ROI is treated as if it contained skin and a PPG signal is extracted from the ROI with this assumption as conventionally done with skin regions.

For the transformation generally any kind of frequency domain transformation, such as a FFT, DCT, wavelet transform, Haar transform, etc. may be used.

According to an embodiment said transformation unit is configured to transform said PPG signal into a spectral signal without phase information, in particular into a power spectrum or an absolute spectrum, i.e. to convert the complex spectrum to a real signal. The output of a Fourier transform is a complex (real and imaginary parts) signal. If the phase information is not of interest, the norm of the complex samples (length of the vector in the complex plane) may be taken, which is often called the absolute spectrum or amplitude spectrum. By squaring these numbers a power spectrum is obtained. It is advantageous because it is desired to discriminate between a pulse (which can simply be modeled of a sinusoid with unknown phase and frequency, but will in the sorted spectrum always appear as a high amplitude in the first (few) bin(s)) and noise (which can be modeled as a random (both amplitude and phase) signal, which will in the (sorted or unsorted) spectrum appear as a broad band of frequencies with the same amplitude). These two sorted spectra are easy to classify.

In another embodiment said sorting unit is configured to divide said spectral signal into two or more spectral sub-signals and to separately sort said sub-signals to obtain sorted spectral sub-signals representing the descriptor. It has been found that such sub-signals even better allow distinguishing e.g. a pulse signal from noise and, thus, skin from non-skin.

Preferably, said sorting unit is configured to divide said spectral signal into an in-band sub-signal covering a first frequency range of said spectral signal and an out-band sub-signal covering the remaining frequency range of said spectral signal and to separately sort said in-band sub-signal and said out-band sub-signal to obtain a sorted in-band sub-signal and a sorted out-band sub-signal representing the descriptor. Hereby, said sorting unit may further be configured to divide said spectral signal such that the in-band sub-signal covers a lower portion of the frequency range of said spectral signal or a portion of the frequency range around a highest frequency peak of said spectral signal. For instance, the in-band can simply be the lower half of an oversampled PPG signal and the out-band can simply be the upper half of the same oversampled PPG signal. In a more sophisticated version, the in-band may be defined as a window around the highest frequency peak, e.g. with half of the total frequency bins, and the out-band then may be defined by the remaining frequency bins. Other choices for separating the frequency bins are possible as well to define a more accurate in-band", e.g. by choosing likely-pulse spectral components (e.g. only the 20% highest peaks in the frequency domain) as in-band and the remaining spectral components as out-band.

In another embodiment said transformation unit is configured to normalize the spectral signal so that the amplitude or energy (depending on the kind of normalization) of the spectrum does not have an influence on the subsequent evaluation. This makes the spectrum substantially independent of pulse and noise amplitudes in skin and non-skin areas, respectively. The normalization may e.g. be implemented by a division L1- or L2-norm. A practical embodiment may comprise resetting the phase spectrum to a constant value for all frequencies and normalizing the amplitude spectrum to obtain a robust classification.

The device may further comprise a control unit for controlling the transformation unit and said sorting unit to perform two or more iterations, wherein the sorted spectral signal output from said sorting unit is used as input PPG signal for the transformation unit in the next iteration. Thus, the iteration acts on the output of the previous iteration, preferably after halving the length of the signal resulting in a multi-scale representation of the spectrum finally used by the classifier. Particularly the first iteration leads to a relatively peaked signal representing the non-tissue due to resetting the phase of the noise frequency components. Preferably, the length of the spectrum is reduced in the different iterations, i.e., the transformation is performed in different scales resulting in the multi-scale representation, wherein the coarser spectrum (with less samples) still describes the same signal, but at a coarser scale.

It has been found that a repetition of the transformation and sorting transforms a (peaked) pulse spectrum into a flat spectrum, while a (relatively flat) noise spectrum is transformed into a peaked spectrum. In the repeated transforms the phase information, the location of the peak, and the amplitude of the spectrum are preferably disregarded. The sorting makes sure that the peak is substantially at the same location improving the classification.

In a further embodiment said classifier is configured to concatenate the sorted spectral signals output from said sorting unit in each iteration and use said concatenated sorted spectral signal as descriptor for classifying said region of interest as skin region of a living being or as non-skin region. In the concatenated sorted spectral signal the peaked portions and flat portions are alternating, wherein the sequence in said alternation is the opposite for a PPG signal from a skin region compared to a PPG signal from a non-skin region. Thus, a very reliable classification can be made based on such a said concatenated sorted spectral signal.

Further, in an embodiment said extraction unit is configured to combine, in particular to average, image data values of a group of pixels of said image data per image frame to obtain said PPG signal from said combined image data values. Hence, the average (combination) over a group of pixels may be taken and the time-evolution of concatenated averages may be considered as the 1D time signal. This improves the reliability of the classification. Basically, a loss of resolution (of the skin-map) is treated for an improved reliability of the classification because the averaging increases the difference between pulse and noise (by making the pulse signal less noisy).

The extraction unit may further be configured to combine, in particular to average, image data values of a group of pixels of said image data per image frame at a wavelength or in a wavelength range to obtain said PPG signal from said combined image data values. Still further, the extraction unit may be configured to combine, per pixel or group of pixels and per image frame, image data values of at least two different wavelength channels as a weighted average to obtain said PPG signal from said combined image data values. Hence, the average over a group of pixels per wavelength (or color) may be taken, and the time-evolution of concatenated averages may be concatenated per wavelength to obtain the 1D time signal. Hereby, the extraction unit may be configured to compute said weights using a normalized blood volume pulse vector signature based method (i.e. a Pbv method), a chrominance based method (i.e. a CHROM method), a blind source separation method (i.e. a BSS method), a principal component analysis (PCA) or an independent component analysis (ICA).

Generally, a PPG signal results from variations of the blood volume in the skin. Hence the variations give a characteristic pulsatility "signature" when viewed in different spectral components of the reflected/transmitted light. This "signature is basically resulting as the contrast (difference) of the absorption spectra of the blood and that of the blood-less skin tissue. If the detector, e.g. a camera or sensor, has a discrete number of color channels, each sensing a particular part of the light spectrum, then the relative pulsatilities in these channels can be arranged in a "signature vector", also referred to as the "normalized blood-volume vector", Pbv. It has been shown G. de Haan and A. van Leest, "Improved motion robustness of remote-PPG by using the blood volume pulse signature", Physiol. Meas. 35 1913, 2014, which is herein incorporated by reference, that if this signature vector is known then a motion-robust pulse signal extraction on the basis of the color channels and the signature vector is possible. For the quality of the pulse signal it is essential though that the signature is correct, as otherwise the known methods mixes noise into the output pulse signal in order to achieve the prescribed correlation of the pulse vector with the normalized color channels as indicated by the signature vector.

Details of the Pbv method and the use of the normalized blood volume vector (called "predetermined index element having a set orientation indicative of a reference physiological information") have also been described in US 2013/0271591 A1, which details are also herein incorporated by reference.

The classifier may further be configured to determine the likelihood that said region of interest is a skin region of a living being, i.e. the classifier does not only issue a binary decision of whether the region of interest is a skin region or not, but also a likelihood that the region of interest is a skin region.

The classifier may be obtained from supervised learning (e.g. AdaBoost, SVM, etc.), taking the samples of the transformed signal as input (e.g. ranked, normalized frequency bins) and outputting a signal (hard (binary) label, or regression values) identifying the likelihood of an image segment to be alive human tissue or not. Further, the classifier may be trained using a dataset of 1D time signals including sinusoids with varying amplitudes, levels of noise, and frequencies in the pulse-rate band to represent the segments containing alive human tissue and noise signals representing segments that do not contain alive human tissue.

The device may further comprise a segmentation unit for segmenting the image frames of said image data, wherein said extraction unit is configured to extract a PPG signal from two or more image frame segments for separate subsequent processing.

The present invention is preferably used in the context of vital signs acquisition by use of the remote PPG technology. For this purpose said imaging unit is preferably configured to acquire a sequence of images of the scene over time, and said device may further comprise a vital signs detector for detecting vital signs of a subject within the scene based on image information from detected skin areas within said sequence of images. Thus, the proposed detection of skin areas may be once or continuously used to detect and/or track skin areas during the acquisition of vital signs.

BRIEF DESCRIPTION OF THE DRAWINGS

These and other aspects of the invention will be apparent from and elucidated with reference to the embodiment(s) described hereinafter. In the following drawings FIGS. 3A and 3B show diagrams illustrating exemplary PPG signals from skin and non-skin regions for different living beings, FIGS. 4A, 4B, 4C, and 4D show diagrams illustrating exemplary signals at the various steps of a method according to an embodiment of the present invention.

DETAILED DESCRIPTION OF THE INVENTION

Figure 1:
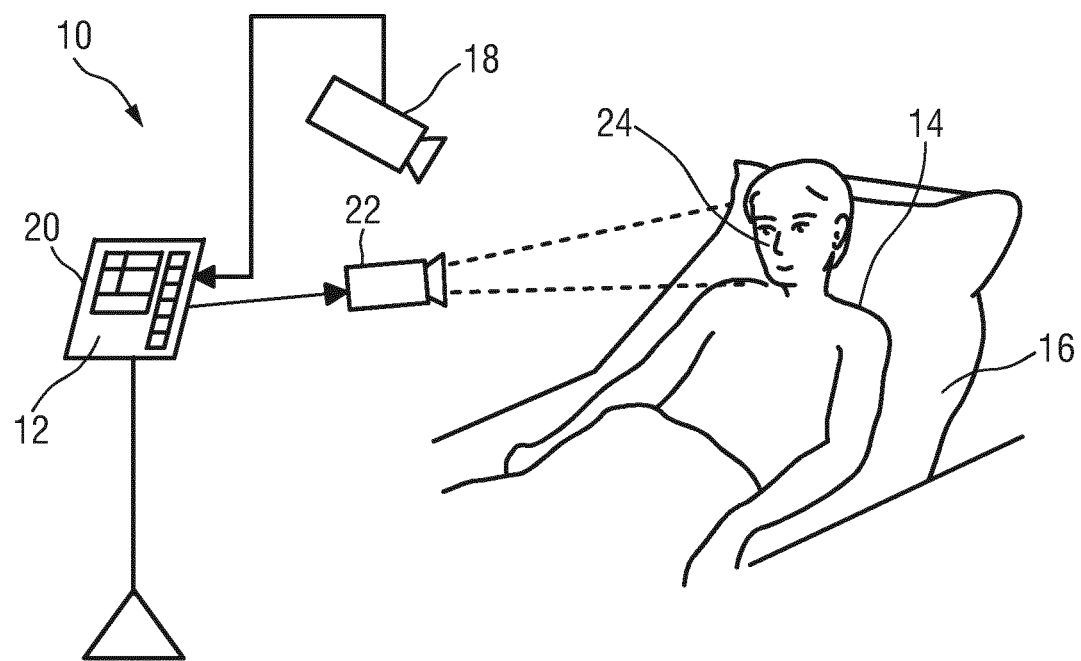
FIG. 1 shows a schematic diagram of a first embodiment of a system according to the present invention.

FIG. 1 shows a schematic diagram of a system 10 according to the present invention including a device 12 for skin detection. The system 10 and device 12 may preferably be used in a device and method for detecting vital signs of a subject 14 from image data including a time sequence of image frames of the subject. The subject 14, in this example a patient, lies in a bed 16, e.g. in a hospital or other healthcare facility, but may also be a neonate or premature infant, e.g. lying in an incubator, or person at home or in a different environment, such as an athlete doing sports.

The imaging unit 18 may include a camera (also referred to as detection unit or as camera-based or remote PPG sensor) for acquiring an image data (also called RGB images, which shall be understood as an image in the wavelength range of visual and/or infrared light) of the scene, in particular for acquiring a sequence of image frames of the subject 14 over time, preferably including skin areas 15 of the subject 14 from which PPG signals can be derived. In an application of the device 12 for obtaining vital signs of the subject 14, the skin area 15 is preferably an area of the face, such as the cheeks or the forehead, but may also be another area of the body with visible skin surface, such as the hands or the arms.

The image frames captured by the imaging may particularly correspond to a video sequence captured by means of an analog or digital photosensor, e.g. in a (digital) camera. Such a camera usually includes a photosensor, such as a CMOS or CCD sensor, which may also operate in a specific spectral range (visible, nIR) or provide information for different spectral ranges, particularly enabling the extraction of PPG signals. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the person. Thereby, an image pixel may correspond to one photosensitive element of a photo-detector and its (analog or digital) output or may be determined based on a combination (e.g. through binning) of a plurality of the photosensitive elements.

When using a camera 18 the system 10 may further optionally comprise an illumination unit 22 (also called illumination source or light source or electromagnetic radiator), such as a lamp or LED, for illuminating/irradiating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength ranges (e.g. green and red or infrared light, or light in a sufficiently large wavelength range covering at least two wavelength channels) may be detected and/or evaluated.

The device 12 is further connected to an interface 20 for displaying the determined information and/or for providing medical personnel with an interface to change settings of the device 12, the camera 18, the illumination unit 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 12, the camera 18 and the interface 20 may work via a wireless or wired communication interface. Other embodiments of the present invention may include a device 12, which is not provided stand-alone, but integrated into the camera 18 or the interface 20.

Figure 2:
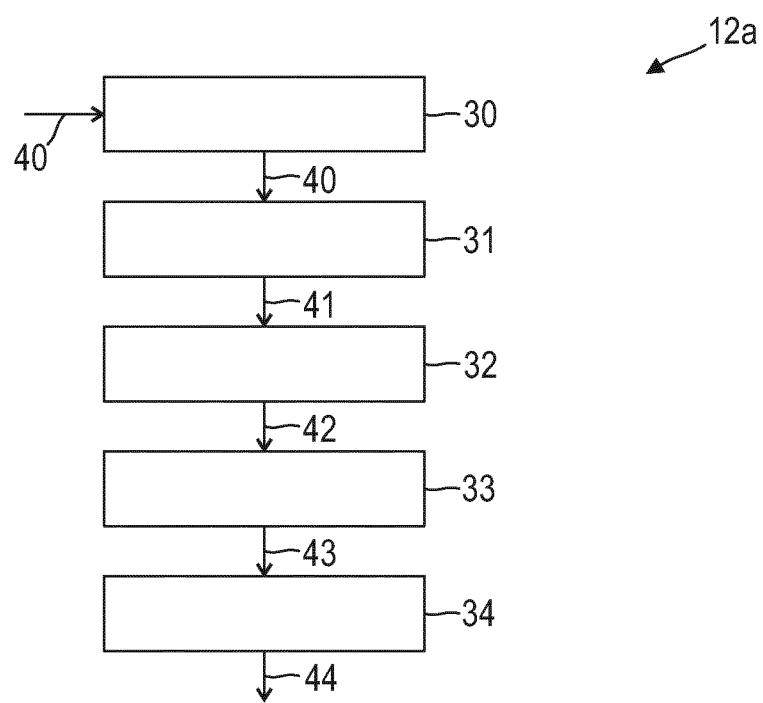
FIG. 2 shows a schematic diagram of a first embodiment of a device according to the present invention.

FIG. 2 shows a schematic diagram of a first embodiment of a device 12a according to the present invention, which may be used as device 12 in the system 10 shown in FIG. 1. For deriving one or more vital signs of the subject 14 a skin area of the subject has to be found in the image data. For this purpose, the proposed device 12a comprises an input interface 30 for obtaining image data 40 of a scene, said image data comprising a time sequence of image frames acquired by the imaging unit 18. An extraction unit 31 extracts a PPG signal 41 from a region of interest of said image data, wherein said region of interest may a single pixel or a group of pixel or an area resulting from a segmentation of one or more image frames. A transformation unit 32 transforms said PPG signal 41 into a spectral signal 42. A sorting unit 33 sorts said spectral signal 42 to obtain a sorted spectral signal 43 representing a descriptor. Finally, a classifier 34 classifies said region of interest as skin region of a living being or as non-skin region based on the descriptor and issues a corresponding classification result 44, which may be a binary decision (e.g. indication that the region of interest is a skin are or not) or a likelihood that the region of interest is a skin area or not.

The units 30 to 34 may be configured as dedicated hardware elements, but may also be configured as processor or computer, which is programmed accordingly. The device 12a may be configured as integrated device including all its elements and units, e.g. in a common housing (e.g. in a common housing of the imaging unit 18) or as distributed device, as shown in FIG. 1, in which the elements and units may be distributed, i.e. implemented as separate elements and units arranged at different positions.

FIGS. 3A and 3B show diagrams illustrating exemplary PPG signals 41 from skin and non-skin regions for different living beings. In particular, FIG. 3A shows a pulse signal 41a from a first subject (e.g. an adult) and a pulse signal 41c from a second subject (e.g. a neonate). As can be seen, the pulse signals from different subjects are different. Further, even the pulse signal from a single subject is time-varying (e.g. in phase). Although the pulse generally has a clear periodic component, there may be variations in amplitude, phase and even frequency (e.g. heart rate variability), and typically the signal will also suffer from sensor noise and may be distorted by subject motion. FIG. 3B shows a noise signal 41b from the first subject (e.g. an adult) and a noise signal 41d from the second subject (e.g. a neonate). As can be seen, noise signals are irregular/erratic signals that cannot be learned, while also pulse signals exhibit significant variability. Hence, one idea is to transform obtained PPG signals into a different representation that allows supervised learning.

Considering pulse and noise as two classes, the transformed representation (e.g. the descriptor) should eliminate three properties in PPG signals. The descriptor should be invariant to phase changes of pulse/noise, i.e. pulse at different moments. Further, the descriptor should not depend on the amplitude of pulse/noise. Still further, the descriptor should be independent of varying frequencies in pulse/noise, i.e. different subjects.

Given above requirements, the following exemplary approach is applied to the PPG signals 41, which is illustrated by use of FIG. 4 showing a diagram illustrating exemplary signals at the various steps of the method according to the present invention. In a first step, spectrum boosting is applied to the PPG signals 41 (for illustration, a pulse signal 41a and a noise signal 41a are shown in FIG. 4A) by the transformation unit 32. Based on the valid assumption that pulse is a periodic signal, the transformation unit 32 transforms the PPG signal 41 from time domain to frequency domain for analysis, for instance by use of a Fourier Transform (FT). The transformed pulse 42a shown in FIG. 4B presents a significant peak in the frequency spectrum, whereas the transformed noise 42b shown in FIG. 4B is an irregular signal that does not show such a pattern. Hereby, the Fourier Transform (or Fast Fourier Transform; FFT) can be replaced by a Discrete Cosine Transform (DCT), a Discrete Sine Transform (DST), a Wavelet Transform, or a Haar Transform, etc.

Using the FT can be written as:

$$\vec{F}^L = \mathcal{F}(\vec{P}^L), \quad (1)$$

with the PPG signal with length $L=2^{n, \{n | \in Z, n \geq 2\}}$ for $\vec{P}^L$ Fourier transform (e.g., L=64); $\mathcal{F}(:)$ denotes the FT operation. The real and imaginary parts of $\vec{P}^L$ contain varying phase information, which can be eliminated by just using the amplitude or power spectrum. Preferably, the power spectrum is used because it generally boosts the frequency peak of pulse and suppresses the noise. Since $\vec{F}^L$ is a mirrored spectrum with half redundancy, it is halved before deriving the power spectrum:

$$S^{L/2} = \vec{F}^{1 \to L/2} \odot \text{conj}(\vec{F}^{1 \to L/2}), \quad (2)$$

where conj(•) denotes the conjugation; $\odot$ denotes the element-wise product. In $S^{L/2}$, the phase information disappear, while the frequency peak of pulse is boosted as compared to that of noise, as shown in FIG. 4B.

In a next step, spectrum normalization may be performed by the transformation unit 32. This normalization makes the spectrum substantially independent of pulse and noise amplitudes in skin/non-skin areas, respectively. The spectrum amplitudes are still variant in $S^{L/2}$, which are normalized as:

$$\bar{S}^{L/2} = \frac{S^{L/2}}{\|S^{L/2}\|_p}, \quad (3)$$

where $\|\bullet\|_p$ denotes the Lp-norm. It can either be the L1-norm or L2-norm. The normalization of the standard deviation is not preferred, since only the absolute energy information shall be illuminated, but the variation should remain within the spectrum for distinguishing pulse and noise. In an exemplary embodiment the L2-norm is used, because it can suppress noise with respect to the total energy. The normalized $\bar{S}^{L/2}$ is independent of spectrum amplitude, whereas the relative energy distribution of its entries is remained, as shown in FIG. 4C for a normalized spectral pulse signal 42a' and a normalized spectral noise signal 42b'.

In a next step, spectrum sorting is performed by the sorting unit 33. Due to the frequency variance, $\bar{S}^{L/2}$ cannot be used for classification yet. However, although different individuals have different heart rates, their pulse frequencies are mostly peaked and concentrated in a certain (lower) band, i.e., [40, 240] beats per minute (bpm), whereas the background (non-skin) signals are usually white noise that spread into the high-frequency band. To this end, the $\bar{S}^{L/2}$ is divided again, e.g. halved into two halves (also called sub-signals), preferably into lower and upper parts to approximate the "in-band" and "out-band" frequencies, where the pulse-related property is implicitly exploited here.

To eliminate the frequency dependency, the divided spectrums are sorted and then concatenated as:

$$\hat{S}^{L/2} = [\text{sort}(\bar{S}^{1 \to L/4}), \text{sort}(\bar{S}^{L/4 \to L/2})], \quad (4)$$

where sort(•) denotes sorting the spectrum entries for example in a descending order of amplitude/energy. In $\hat{S}^{L/2}$, the frequency variance in pulse and noise are eliminated, but their essential differences in the lower band and upper band are preserved, as shown in FIG. 4D showing a sorted spectral pulse signal 43a and a sorted spectral noise signal 43b. Hence, in this step a ranking (sorting) procedure is essentially performed acting on the frequency bins.

An essential difference between the proposed approach and known approaches is that known approaches only use a single value (e.g., normalized spectrum peak) to separate pulse and noise, whereas the proposed approach exploits all the entries in a sorted spectrum for classification, which is in fact a shape descriptor. Essentially, according to the proposed approach the phenomenon is exploited that the energy of a pulse signal (in the ranked frequency spectrum) drops faster than the energy of the ranked noise spectrum. With a trained classifier using these ranked spectra as input an optimal decision can be obtained. In other words, in the above illustrated first embodiment the sorted spectral signals 43a, 43b are used by the classifier 34 to decide if the respective region of interest in the original image data is a skin region of a living being or is a non-skin region.

Figure 5:
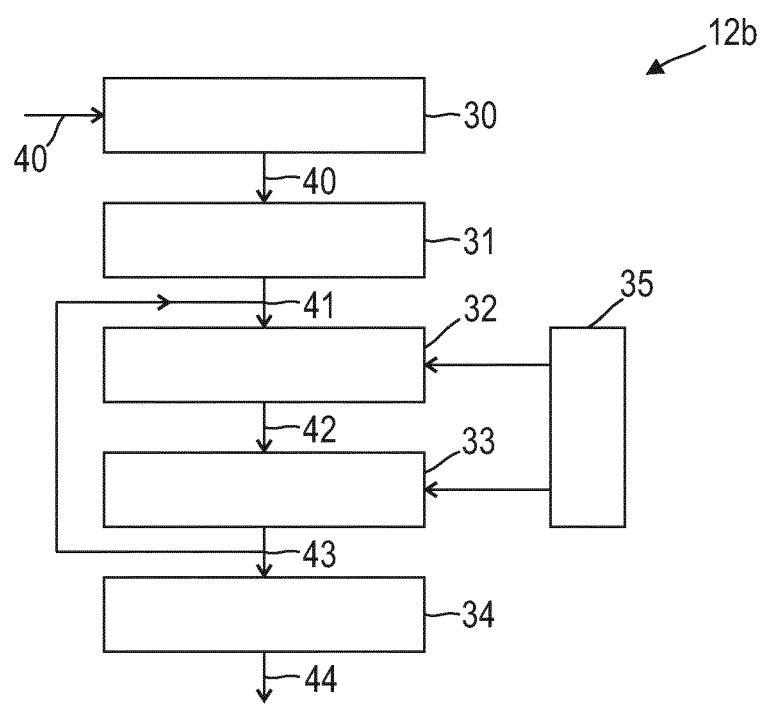
FIG. 5 shows a schematic diagram of a second embodiment of a device according to the present invention.

FIG. 5 shows a schematic diagram of a second embodiment of a device 12b according to the present invention. In this embodiment a control unit 35 is provided for controlling said transformation unit 32 and said sorting unit 33 to perform two or more iterations, wherein the sorted spectral signal 43 output from said sorting unit 33 is used as input PPG signal 41' for the transformation unit 32 in the next iteration. Thus, according to this embodiment a multiscale iteration may be performed as will be explained in the following.

With the first embodiment of the device 12a a transformed signal $\hat{S}^{L/2}$ is obtained given the input PPG signal $\vec{P}^L$, where pulse and noise have self-unified but mutually different interpretations. If the descriptor for pulse and noise is compared, the pulse-descriptor has a salient feature (e.g., peak at first location), whereas the noise does not. To obtain better classification performance, the descriptors from different classes require large between-class variance, i.e. pulse and noise are easily distinguishable. This can be improved by iterating the procedure (boost, normalize, sort). Now the relatively flat noise spectrum translates into a clear peak, while the peaked pulse spectrum translates into a relatively flat result. The two iterations combined provides an anti-phase pattern between two classes, which lead to easier separation.

Figure 6:
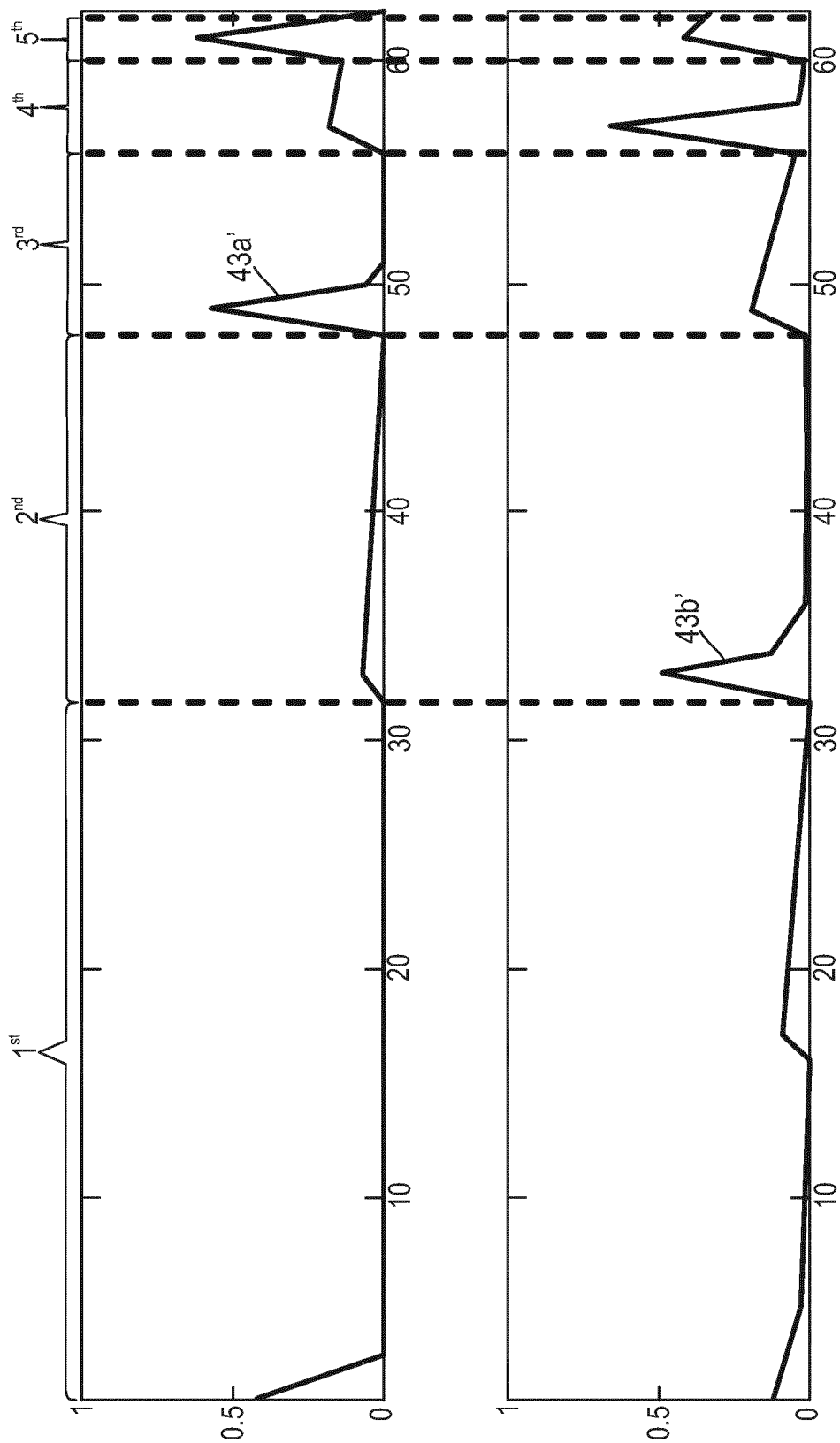
FIG. 6 shows a diagram illustrating descriptors related to the processing according to the second embodiment.

Similarly, the same transformation is further iterated on the transformed signals one or more times. The newly generated patterns in pulse and noise occur in an opposite order, i.e., "peak-flat-peak" versus "flat-peak-flat", as shown in FIG. 6 for an obtained pulse signal descriptor 43a' and a noise signal descriptor 43b'. In the illustrated example the sorted spectral signals of five iterations are concatenated.

In this way, a longer descriptor X is thus created to collect/concatenate the iteratively transformed signals in different scales:

$$X_{i+1}=[X_i, \hat{S}_i^{L/(2\times i)}], \{i|i \in \mathbb{Z}, 1 \leq i \leq \log_2(L)\}, \quad (5)$$

where $\hat{S}_i^{L/(22\times i)}$ is the transformed signal in i-th iteration with length L/(2×i). When the iteration is finished, the complete descriptor may further be normalized by L2-norm. In fact, the proposed descriptor is built on the hypothesis that multiscale iterations can improve the discriminativity of the descriptor. Such hypothesis has been experimentally verified.

Thus, the iteration acting on the output of the previous iteration is preferably started after halving the length of the signal. In this case, the iteration makes a multi-scale representation of the spectrum available to the classifier. Particularly the first iteration leads to a relatively peaked signal representing the non-tissue, due to the elimination of the phase in the noise frequency components. For this reason, at least two sequential transforms may be performed: FFT—delete phase—normalize—rank—FFT—delete phase—normalize—rank, where for efficiency the second transform may act on the half spectrum obtained from the first iteration.

Figure 7A:
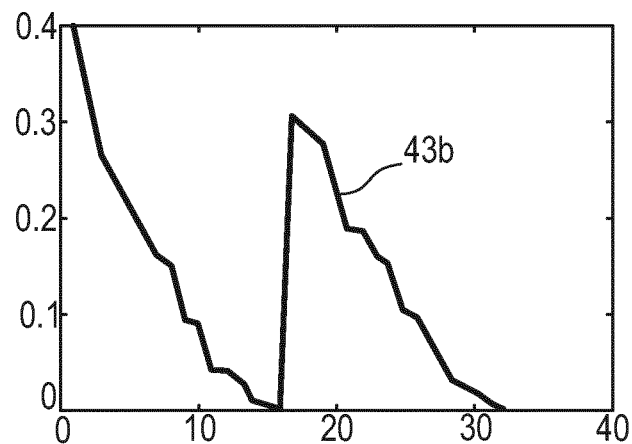
FIGS. 7A and 7B show diagrams illustrating descriptors related to the processing according to a third embodiment of the present invention.
Figure 7B:
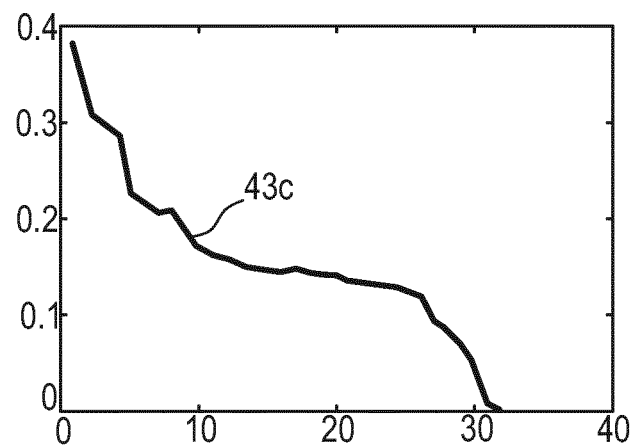

Furthermore, the discriminativity between pulse and noise representations may be further improved. In an embodiment the flat/peaked patterns in the transformed descriptor (43a', 43b') can be made even more flat/peaked. Equation (2) uses a single signal to derive the power spectrum. This may be improved by using two temporally adjacent signals (with one frame shifted). It mainly benefits the noise class: the conjugation of two noise signals induces negative entries in the real part of the power spectrum. This is due to the high-frequency components in noise signals, i.e., background (non-skin) signals are mostly white noise and thus exploited here. Subtracting the minimal negative value in the spectrum can make the noise descriptor more flat in the first iteration, as shown in FIG. 7B showing the thus obtained noise descriptor 43c compared to the original noise descriptor 43b shown in FIG. 7A (and FIG. 4D). Therefore, in such an embodiment the boosting step may be modified by conjugating two temporally adjacent signals (with one frame shifted) instead of a single signal.

As illustrated above, in a preferred embodiment, it is proposed to disregard the phase information, but to take the absolute spectrum or the power spectrum.

Preferably, the ranking is done twice: an in-band ranking and an out-band ranking. In-band can simply be the lower half of an oversampled signal, and out-band the upper-half. However, in a more sophisticated version, in-band may be defined as a window around the highest frequency peak, e.g. with half of the total bin-number, out-band then is formed by the remaining frequency bins.

The classification may use a classifier obtained from supervised learning (e.g. AdaBoost, SVM, etc.), taking the samples of the transformed signal as input (e.g. ranked, normalized frequency bins without phase information) and outputting a signal (hard (binary) label, or regression values) identifying the likelihood of an image segment to be alive-human-tissue or not. Although the supervised learning may use actual data obtained from skin and non-skin surfaces, good performance has been obtained by training the classifier using a dataset of 1D time signals including sinusoids with varying amplitudes, levels of noise, and frequencies in the pulse-rate band to represent the segments containing alive human tissue and noise signals (zero-mean Gaussian, or uniform, etc.) representing segments that do not contain alive-human-tissue.

Still further, the proposed method may be applied to classify image regions obtained from segmentation, where possibly motion tracking may be used to track individual segments over time in successive image.

The present invention is preferably applied in the field of rPPG for the acquisition of vital signs of the person. Thus, images obtained by an imaging unit are not only used for detecting skin areas as explained above, but from detected (and preferably tracked, also by use of the present invention) skin areas PPG signals are derived, which are used for deriving vital signs of the person, such as heartbeat, SpO2, etc. The imaging unit 18 is at least sensitive at the wavelength(s) or wavelength ranges, in which the scene is illuminated (by ambient light and/or by illumination), but may be sensitive for other wavelengths as well, in particular if required for obtaining the desired vital signs.

In another embodiment of the present invention, the proposed analysis for skin detection can be combined with another method for skin detection, e.g. the analysis of chrominance or temporal pulsatility of structured light reflected from the skin area as generally known. The method may comprise further steps and may be modified as explained above for the various embodiments of the device and as disclosed herein.

The proposed device and method can be used for continuous unobtrusive monitoring of PPG related vital signs (e.g. heartbeat, SpO2, respiration), and can be used in NICU, Operation Room, or General Ward. The proposed device and method can be also used for personal health monitoring. Generally, the present invention can be used in all applications where skin needs to be detected in an image of a scene and needs particularly be distinguished from non-skin.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for skin detection comprising:
    an input interface for obtaining image data of a scene, said image data comprising a time sequence of image frames,
    an extraction unit for extracting a photoplethysmography, PPG, signal from a region of interest of said image data,
    a transformation unit for transforming said PPG signal into a spectral signal,
    a sorting unit configured to divide said spectral signal into an in-band sub-signal covering a first frequency range of said spectral signal and an out-band sub-signal covering the remaining frequency range of said spectral signal and to separately sort said in-band sub-signal and said out-band sub-signal to obtain a sorted in-band sub-signal and a sorted out-band sub-signal representing the descriptor, and
    a classifier for classifying said region of interest as one of a skin region of a living being or a non-skin region based on the descriptor.

2. The device as claimed in claim 1, wherein said transformation unit is configured to transform said PPG signal into a spectral signal without phase information, in particular into one of a power spectrum or an absolute spectrum.

3. The device as claimed in claim 1, wherein said sorting unit is configured to divide said spectral signal such that the in-band sub-signal covers one of a lower portion of the frequency range of said spectral signal or a portion of the frequency range around a highest frequency peak of said spectral signal.

4. The device as claimed in claim 1, wherein said transformation unit is configured to normalize the spectral signal.

5. The device as claimed in claim 1, further comprising a control unit for controlling said transformation unit and said sorting unit to perform two or more iterations, wherein the sorted spectral signal output from said sorting unit is used as input PPG signal for the transformation unit in the next iteration.

6. The device as claimed in claim 1, wherein said classifier is configured to concatenate the sorted spectral signals output from said sorting unit in each iteration and use said concatenated sorted spectral signal as descriptor for classifying said region of interest as one of a skin region of a living being or a non-skin region.

7. The device as claimed in claim 1, wherein said extraction unit is configured to combine, in particular to average, image data values of a group of pixels of said image data per image frame to obtain said PPG signal from said combined image data values.

8. The device as claimed in claim 1, wherein said extraction unit is configured to combine, in particular to average, image data values of a group of pixels of said image data per image frame at a wavelength or in a wavelength range to obtain said PPG signal from said combined image data values.

9. The device as claimed in claim 1, wherein said extraction unit is configured to combine, per pixel or group of pixels and per image frame, image data values of at least two different wavelength channels as a weighted average to obtain said PPG signal from said combined image data values.

10. The device as claimed in claim 9, wherein said extraction unit is configured to compute said weights using a normalized blood volume pulse vector signature based method, a chrominance based method, a blind source separation method, a principal component analysis or an independent component analysis.

* * * * *